(12) United States Patent
Wang et al.

(10) Patent No.: US 7,846,719 B2
(45) Date of Patent: Dec. 7, 2010

(54) EXPRESS SYSTEM OF SOLUBLE GLUTAMINYL CYCLASE

(75) Inventors: Andrew H.-J. Wang, Taipei (TW); Kai-Fa Huang, Taipei (TW)

(73) Assignee: Academia Sinica, Taipei (TW)

( * ) Notice: Subject to any disclaimer, the term of this patent is extended or adjusted under 35 U.S.C. 154(b) by 0 days.

(21) Appl. No.: 11/331,704

(22) Filed: Jan. 13, 2006

(65) Prior Publication Data

US 2007/0281338 A1   Dec. 6, 2007

(51) Int. Cl.
  *C12N 15/00*   (2006.01)
  *C12N 1/20*   (2006.01)
  *C12P 21/04*   (2006.01)

(52) U.S. Cl. ............................. 435/320.1; 435/252.33; 435/71.1

(58) Field of Classification Search ........................ None
See application file for complete search history.

(56) References Cited

U.S. PATENT DOCUMENTS

2003/0013177 A1*  1/2003  Ebens et al. ................ 435/196

OTHER PUBLICATIONS

Novagen (pET-42b+ vector map, Retrieved from the Internet <URL: http://www.emdbiosciences.com/docs/docs/PROT/TB240.pdf>).*
Novagen pET 43.1 (Retrieved from the Internet <URL: http://www.emdbiosciences.com/docs/docs/PROT/TB288.pdf>, published on Sep. 2000).*
Novagen pET 32Xa/LIC (Retrieved from the Internet <URL: http://www.emdbiosciences.com/docs/docs/PROT/TB161.pdf>, published on Dec. 1998).*
Harrison (Expression of soluble heterologous proteins via fusion with NusA protein, inNovations, 11, published on Jun. 2000).*
Terpe (Overview of tag protein fusions: from molecular and biochemical fundamentals to commercial systems, Appl Microbiol Biotechnol (2003) 60:523-533).*
McCormick et al. (inNovations 5, Aug. 1996, Retrieved from the Internet <URL: http://www.emdbiosciences.com/docs/docs/LIT/inno05-001.pdf>).*
pET 16b (Retrieved from the Internet <URL: http://www.emdchemicals.com/life-science-research/pet-16b-dna/EMD_BIO-69662/p_2tOb.s1OkacAAAEjWhl9.zLX?attachments=USP>, published on Feb. 2000).*
Bateman, Jr., et al., "Evidence for Essential Histidines in Human Pituitary glutaminyl Cyclase," Biochemistry, vol. 40, pp. 11246-11250 (2001).
Schilling, et al., "Heterologous Expression and Characterization of Human Glutaminyl Cyclase: Evidence for a Disulfide Bond with Importance for Catalytic Activity," Biochemistry, vol. 41, pp. 10849-10857 (2002).
Booth, et al.., "Human Pituitary Glutaminyl Cyclase: Expression in Insect Cells and Dye Affinity Purification," Protein Expression and Purification, vol. 32, pp. 141-146 (2003).
Schilling, et al., "Glutaminyl Cyclases Unfold Glutamyl Cyclase Activity Under Mild Acid Conditions," FEBS Letters, vol. 563, pp. 191-196 (2004).
Huang, et al., "Cloning, Expression, Characterization, and Crystallization of a Glutaminyl Cyclase from Human Bone Marrow: A single Zinc Metalloenzyme," Protein Expression and Purification, vol. 43, pp. 65-72 (2005).
Busby, Jr., et al., "An Enzyme(s) That Converts Glutaminyl-peptides into Pyroglutamyl-peptides," The Journal of Biological Chemistry, vol. 262, No. 18, pp. 8532-8536 (1987).
Huang, et al., "Crystal Structures of Human Glutaminyl Cyclase, an Enzyme Responsible for Protein N-terminal Pyroglutamate Formation," PNAS, vol. 102, No. 37, pp. 13117-13122 (2005).

* cited by examiner

*Primary Examiner*—Suzanne M Noakes
*Assistant Examiner*—Jae W Lee
(74) *Attorney, Agent, or Firm*—Panitch Schwarze Belisario & Nadel LLP

(57) ABSTRACT

A vector for expressing a soluble glutaminyl cyclase (QC) in bacterial cells is described. The vector contains a sequence encoding a fusion QC, which has a fusion protein tag selected from a Nus protein tag or a thioredoxin (Trx) tag, a QC, and a linker having at least one $(His)_x$-tag between the QC and the fusion protein tag, in which x is an integer of at least 6. Methods for expressing a soluble glutaminyl cyclase (QC) by the vector are also described.

8 Claims, 4 Drawing Sheets

EXPRESS SYSTEM OF SOLUBLE GLUTAMINYL CYCLASE

BACKGROUND OF THE INVENTION

The present invention relates generally to an expression system of soluble glutaminyl cyclase (QC).

Glutaminyl cyclases (QCs) (EC 2.3.2.5.) are acyltransferases responsible for the conversion of the protein N-terminal glutaminyl residue into pyroglutamic acid (pGlu) with the concomitant liberation of ammonia. This cyclization reaction is important during the maturation of numerous neuropeptides and cytokines, such as thyrotropin-releasing hormone (TRH), godadotropin-releasing hormone (GnRH) and monocyte chemotactic protein-2 (MCP-2), in the secretory pathway. The role of pGlu on these bioactive peptides is believed to be in developing the proper conformation of the peptides in order to bind to their targets and/or protecting the peptides from exopeptidase degradation.

In humans, the abberant formation of pGlu may be related to some pathological processes, such as osteoporosis and amyloidotic diseases. The plaque forming peptides, e.g., AβN3(pGlu)-40/42, seem to be directly correlated with the severity and progression of the amyloidotic diseases, such as Alzheimer's disease (AD) and Down's syndrome (DS). The pGlu on these plaque-forming peptides is converted from a glutamyl residue, and contributes to the hydrophobicity and proteinase resistance of these peptides. Such a glutamyl-to-pGlu conversion was demonstrated to be also catalyzed by human QC in vitro [S. Schilling, et al., "Glutaminyl cyclases unfold glutamyl cyclase activity under mild acid conditions," *FEBS Lett.* 563, 191-196 (2004)].

To date, although functional human QC has been expressed in yeast and insect cell systems, expression of the protein still encounters problems with insolubility, low recovery and heterogeneity of the protein [S. Schilling, et al., "Heterologous expression and characterization of human glutaminyl cyclase: evidence for a disulfide bond with importance for catalytic activity," *Biochemistry* 41, 10849-10857 (2002); R. E. Booth, et al., "Human pituitary glutaminyl cyclase: expression in insect cells and dye affinity purification," *Protein Expression &. Purification* 32, 141-146 (2003)].

BRIEF SUMMARY OF THE INVENTION

In one aspect, the invention provides a vector for expressing soluble glutaminyl cyclase (QC), which comprises a sequence encoding QC, a fusion protein tag upstream of the sequence encoding QC, and a linker region having at least one $(His)_x$-tag between the sequence encoding QC and the fusion protein tag, wherein x is an integer of at least 6.

Another aspect of the invention provides a vector for expressing soluble glutaminyl cyclase (QC), which comprises a sequence encoding QC, a Nus protein tag upstream of the sequence encoding QC, a thrombin cleavage site between the sequence encoding QC and the Nus protein tag, a S protein tag between the thrombin cleavage site and the Nus protein tag, a $(His)_6$ tag downstream of the Nus protein tag and a $(His)_6$ tag adjacent to the 3' end of the sequence encoding QC.

A further aspect of the invention provides a vector for expressing soluble glutaminyl cyclase (QC), which comprises a sequence encoding QC, a thioredoxin (Trx) tag upstream of the coding sequence of QC, a Factor Xa cleavage site between the Trx tag and the sequence encoding QC, a $(His)_6$ tag downstream of the Trx tag and a $(His)_6$ tag adjacent to the 5' end of the Factor Xa cleavage site.

In another aspect, the invention provides a method for expressing soluble glutaminyl cyclase (QC) in a Nus-protein tagged vector. The method involves expressing the vector in a cell system; lysing the cells to obtain a protein lysate containing the QC; purifying the QC from the protein lysate containing the QC through a Ni-affinity chromatography with a first buffer comprising approximately 10 mM imidazole; eluting the lysate by a linear gradient of 0 to 100% of a second buffer comprising approximately 300 mM imidazole on the first buffer; treating the eluate with thrombin against a third buffer free of imidazole to obtain a digested solution; passing the digested solution through an S protein agarose column; and purifying glutaminyl cyclase through a Ni-affinity chromatography.

In a final aspect, the invention provides a method for expressing soluble glutaminyl cyclase (QC) in a Trx-tagged vector. The method comprises expressing the vector in a cell system; lysing the cells to obtain a protein lysate containing the QC; purifying the QC from the protein lysate containing the QC through a Ni-affinity chromatography with a fourth buffer comprising approximately 20 mM imidazole; eluting the lysate by a linear gradient of 0 to 100% of a fifth buffer comprising approximately 250 mM imidazole on the fourth buffer; treating the eluate with Factor Xa against a sixth buffer free of imidazole to obtain a digested solution; and eluting the digested solution with a linear gradient of 0 to 30% of the fifth buffer on the sixth buffer.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Definitions

Figure 1A:
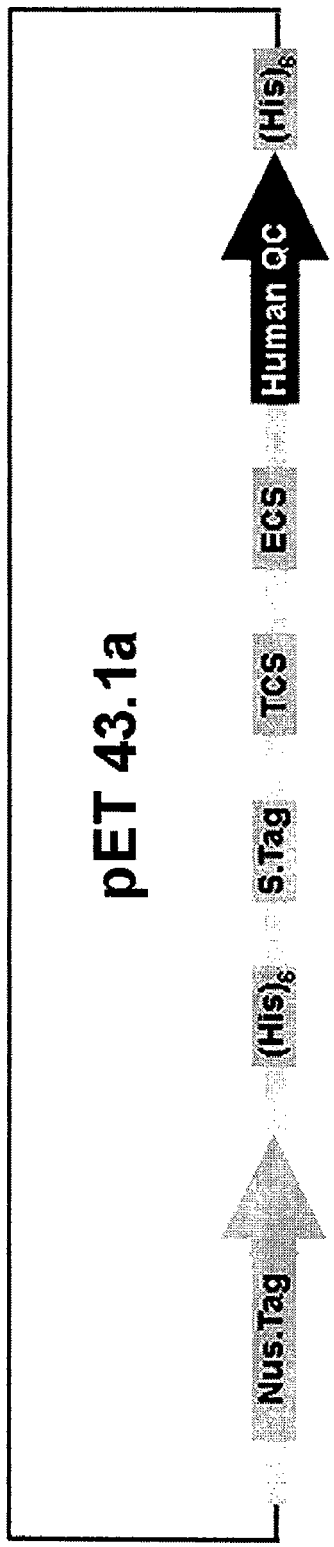
FIG. 1A is a schematic diagram illustrating a vector construct according to one embodiment of the present invention.

To facilitate the understanding of the invention, a number of terms are defined below.

The articles "a" and "an" are used herein to refer to one or more than one (i.e. to at least one) of the grammatical object of the article. By way of example, "an element" means one element or more than one element.

A "vector" is refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses.

A "primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as DNA polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but needs not reflect the exact sequence of the template. In such a case, specific hybridization of the primer to the template depends on the stringency of the hybridization conditions. Primers can be labeled with e.g., chromogenic, radioactive, or fluorescent moieties and used as detectable moieties.

A "tag" is generally referred to as a gene sequence that encodes for a protein tag acting as an indicator or marker to facilitate recognition by other molecules. Recognition of the protein tag, which can be covalently attached to the target molecule, may result in modification, sequestration, transport or degradation of the molecule. In the affinity purification process, the protein tag specifically interacts with an affinity resin and binds the tagged protein, whereas other proteins are not bound to the resin. This then allows a simple purification by washing the resin with a buffer and releasing the tagged protein from the resin.

A "restriction site" is a portion of a double-stranded nucleic acid which is recognized by a restriction endonuclease. A portion of a double-stranded nucleic acid is "recognized" by a restriction endonuclease if the endonuclease is capable of cleaving both strands of the nucleic acid at the portion when the nucleic acid and the endonuclease are contacted.

The term "upstream" herein refers to a region 5' to a point of reference or a region toward the 5' end of the strand in the vector.

The term "downstream" herein refers to a region 3' to a point of reference or a region toward the 3' end of the strand in the vector.

The present invention provides a vector for expressing soluble glutaminyl cyclase, which comprises a sequence encoding glutaminyl cyclase (QC), a fusion protein tag upstream of the sequence encoding QC, and a linker having at least one $(His)_x$-tag between the sequence encoding QC and the fusion protein tag, wherein x is an integer of at least 6. The linker region is not limited to include specific sequences described herein. Rather, other DNA sequences, such as fusion protein tags, cleavage sites and repeating sequences may also be included in the linker region to improve the solubility of the QC, depending on the subsequent expression and purification methods used. The linker, which preferably has a length of at least 55 amino acid residues, is inserted between the sequence encoding QC and the fusion protein tag.

In one embodiment of the invention, the sequence encoding QC is a human QC which was amplified from bone marrow cDNA library using the primers of the following sequences: 5'-GGCTGGGAGAGATGGCAGGCGGAA-3' (SEQ ID NO:1) and 5'-GGATAGATGTTTCCACACAG-CATT-3' (SEQ ID NO:2), respectively.

In another embodiment of the invention, the vector comprises two $(His)_6$-tags arranged adjacent to the sequence encoding QC. However, the vector may also include a plurality of $(His)_6$-tags spanning between the sequence encoding QC and the fusion protein tag.

In accordance with one embodiment of the invention, the fusion protein tag may be, for example, a Nus protein tag in a Nus-tagged expression vector, such as pET 43.1a (Novagen, Madison, Wis.). The vector also comprises a thrombin cleavage site (TCS) upstream of the coding sequence of QC, which is preferably arranged between the sequence encoding QC and the Nus protein tag.

In accordance with a further embodiment, the vector further comprises a S protein tag between the TCS and the Nus protein tag.

In a preferred embodiment, the vector is constructed in such a way that one $(His)_6$-tag is introduced at the 3'-end of the sequence encoding QC, and the other $(His)_6$-tag is introduced downstream of Nus protein tag and is between the S protein and the Nus protein tag, as shown in FIG. 1A.

In accordance with another embodiment of the invention, the fusion protein tag may be, for example, a thioredoxin (Trx) tag in a Trx-tagged expression vector, such as pET 32a (Novagen, Madison, Wis.). The vector also comprises a Factor Xa cleavage site adjacent to the 5' end of the coding sequence of QC.

Figure 1B:
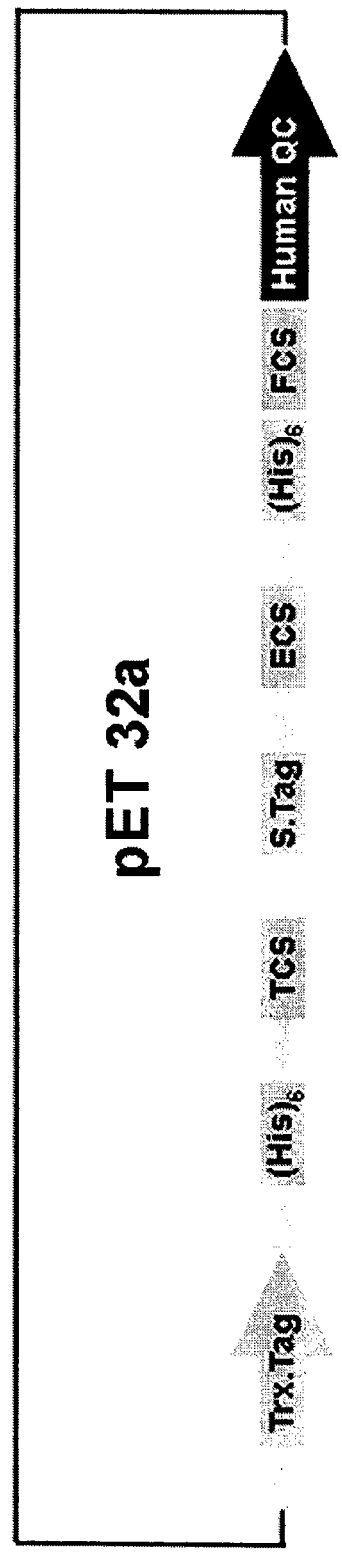
FIG. 1B is a schematic diagram illustrating a vector construct according to another embodiment of the present invention.

In another preferred embodiment, the vector is constructed in such a way that both $(His)_6$-tag are introduced at the 5'-end of the sequence encoding QC and between the sequence encoding QC and the Trx tag. Specifically, one $(His)_6$ tag is arranged adjacent to the 5' end of the Factor Xa cleavage site and the other $(His)_6$ tag is arranged adjacent to the 3' end of the Trx tag, as shown in FIG. 1B.

In addition, the vector may also include other protease cleavage sites, such as thrombin cleavage site, factor Xa cleavage site and enterokinase cleavage site, as well as other fusion protein tags arranged upstream of the sequence encoding QC for improving the subsequent proteolytic digestion and purification processes.

The invention also provides a method for expressing QC which comprises expressing the vector of the invention in a cell system whereby a protein lysate containing QC is obtained, and purifying the protein lysate containing QC. The cell system comprises *Escherichia coli* (*E. coli*) cells, and more preferably *E coli* BL21 (DE3) cells. The protein lysate containing QC is harvested and subjected to purification. Any standard methodology can be used for purification according to the invention.

In one embodiment of the invention, Ni-affinity chromatography is performed by passing the lysate-containing QC through a Ni-NTA column. According to the embodiment of the invention, the Nus-fusion QCs and thioredoxin-fusion QCs are eluted from the Ni-NTA column.

The eluates collected from the Ni-NTA column purification may further be collected and digested. Depending on the number and type of cleavage sites constructed in the vector, the purified protein containing QC may be digested with a protease, such as thrombin, Factor Xa, or both in digesting step(s) to eliminate the Nus and thioredoxin fusion proteins from QC in a digested solution.

After the digesting step(s), the QC in the digested solution may be collected and further purified. Since the QC molecule contains 16 (about 5%) histidine residues, the protein could bind weakly to the Ni-NTA resin. Therefore, Ni-affinity chromatography is performed to purify the QC. In the present invention, any purification methods commonly used in the field that involve binding to the histidine residues of the QC may be used.

According to one embodiment of the invention, the QC expressed in the vector as shown in FIG. 1A may be purified by the process involving:

purifying the protein lysate through a first Ni-affinity chromatography column with a first buffer comprising approximately 10 mM imidazole;

eluting the lysate by a linear gradient of 0 to 100% of a second buffer containing 300 mM imidazole on the first buffer;

treating the eluate with thrombin against a third buffer free of imidazole to obtain a digested solution; and passing the digested solution through an S protein-agarose column.

The process according to the invention may further comprise a step of purifying glutaminyl cyclase through a second Ni-affinity chromatography column.

In a preferred embodiment of the invention, the process for purifying the QC expressed in the vector as shown in FIG. 1A comprises the steps of (1) treating the *E. coli* BL21 (DE3) cells with first centrifugation;
(2) freezing the cells at approximately −80° C.;
(3) placing the cells in a first buffer consisting essentially of approximately 300 mM NaCl and approximately 10 mM imidazole in approximately 50 mM sodium phosphate;
(4) lysing the cells by French Press;
(5) treating the cells with second centrifugation;
(6) loading the supernatant onto a Ni-NTA column and then by eluting with a linear gradient in the range of 0 to 100% of a second buffer, consisting essentially of approximately 300 mM NaCl and approximately 300 mM imidazole in approximately 50 mM sodium phosphate, on the first buffer;
(7) treating the eluted Nus-fusion glutaminyl cyclase with thrombin of approximately 0.1 unit/ml in a dialysis bag against a third buffer consisting essentially of 300 mM NaCl in 50 mM sodium phosphate at approximately 25° C. overnight to obtain a digested solution;
(8) loading the digested solution on an S protein-agarose column, resulting in an un-tagged glutaminyl cyclase eluted from a column; and
(9) loading the un-tagged glutaminyl cyclase on a Ni-NTA column to obtain the purified QC.

According to another embodiment of the invention, the QC expressed in the vector as shown in FIG. 1B may be purified by the process characterized by the steps of:

purifying the protein lysate through a first Ni-affinity chromatography column with a fourth buffer comprising approximately 20 mM imidazole;

eluting the lysate by a linear gradient of 0 to 100% of a fifth buffer comprising approximately 250 mM imidazole on the fourth buffer; and further eluting with a linear gradient of 0 to 30% of the fifth buffer on a sixth buffer free of imidazole.

In an preferred embodiment of the invention, the process for purifying a QC expressed in the vector as shown in FIG. 1B comprises the steps of (1) treating the *E. coli* BL21 (DE3) cells with first centrifugation;
(2) freezing the cells at approximately −80° C.;
(3) placing the cells in a fourth buffer consisting essentially of approximately 150 mM NaCl and approximately 20 mM imidazole in approximately 50 mM Tris-HCl;
(4) lysing the cells by French Press;
(5) treating the cells with second centrifugation;
(6) loading the supernatant onto a Ni-NTA column and then by eluting with a linear gradient in the range of 0 to 100% of a fifth buffer, consisting essentially of approximately 300 mM NaCl and approximately 250 mM imidazole in approximately 50 mM Tris-HCl, on the fourth buffer;
(7) treating the thioredoxin-fusion glutaminyl cyclase with Factor Xa of approximately 0.2 unit/ml in a dialysis bag against a sixth buffer consisting essentially of 150 mM NaCl in 50 mM Tris-HCl at approximately 25° C. for approximately 2 days to obtain a digested solution; and
(8) loading the digested solution onto a Ni-NTA column with a linear gradient in the range of 0 to 30% of the fifth buffer on the sixth buffer, consisting essentially of 150 mM NaCl in 50 mM Tris-HCl to obtain the purified QC.

The invention will now be described in further detail with reference to the following specific, non-limiting examples.

Example 1

Construction of Expression Vectors

Using the primers, 5'-GGCTGGGAGAGATGGCAG-GCGGAA-3' (SEQ ID NO:1) and 5'-GGATAGATGTTTC-CACACAGCATT-3' (SEQ ID NO:2), which are referred to as the 5'- and 3'-noncoding regions of human pituitary QC, respectively, the human QC cDNA was amplified from a commercial bone marrow cDNA library (Clontech, Palo Alto, Calif.) by polymerase chain reaction (PCR). The DNA fragment on the PCR product corresponding to the coding region of human QC (Ala33-Leu361) was re-amplified and inserted into a pET-43.1a expression vector (Novagen, Madison, Wis.) via EcoR I and Xho I cloning sites. A protein cleavage site, such as thrombin cleavage site (TCS), was introduced upstream of the sequence encoding human QC to facilitate protein purification by protein cleavage. The resulting construct, as shown in FIG. 1A, contains two $(His)_6$-tags at the N- and C-terminal sites of human QC. In addition, a pET-32a-based vector was constructed, shown in FIG. 1B. With the initial PCR product as a template, a further PCR was carried out in order to amplify the sequence encoding human QC and to introduce a $(His)_6$-tag and a Factor Xa cleavage site (FCS) into the 5'-end of the coding region of human QC. The PCR product was ligated into the pET-32a expression vector (Novagen, Madison, Wis.) via the Hind III-Xho I sites. Furthermore, the expression vectors above were constructed with additional DNA sequences, such as an enterokinase cleavage site (required for digestion in the subsequent purification process) and other fusion protein tags (such as an S protein tag), to facilitate the subsequent protein purification process.

Example 2

Protein Expression and Purification

The constructed expression vectors were transformed into *E. coli* BL21 (DE3) cells (Novagen, Madison, Wis.). The bacteria were grown in LB media containing 200 μg/ml ampicillin at 37° C. until a cell density of 0.6 to 0.8 $OD_{600}$ was reached. The cultures were induced with 1 mM isopropyl-β-D-thiogalactopyranoside (IPTG) for 2 or 4 days at 20° C. The cells were harvested by centrifugation at 6000 rpm, followed by freezing at −80° C.

In the case of pET 43.1a-based vector, the frozen bacterial pellet was resuspended in buffer A (300 mM NaCl and 10 mM imidazole in 50 mM sodium phosphate, pH 8.0) and lysed by French Press. The lysate was clarified by centrifugation at 22000 revolution per minutes (rpm) for 1 hour and then loaded onto a Ni-NTA (Amersham Pharmacia, Uppsala, Sweden) column pre-equilibrated with buffer A. After the column was washed with buffer A, the Nus-fusion QCs were eluted by a linear gradient of 0 to 100% buffer B (similar to buffer A but containing 300 mM imidazole) on buffer A. The eluates were pooled and then digested with thrombin (0.1 unit/ml) (Novagen, Madison, Wis.) in a dialysis bag dialyzed against buffer C (300 mM NaCl in 50 mM sodium phosphate, pH 8.0) at 25° C. overnight. The cleaved Nus proteins were eliminated from the digests by employing an S protein-agarose (Novagen, Madison, Wis.) column, and then the QCs in the flow-throughs were pooled and further purified by a Ni-NTA column.

For the construct of pET 32a, buffers A and B above were replaced with buffer D (150 mM NaCl and 20 mM imidazole in 50 mM Tris-HCl, pH 8.0) and buffer E (similar to buffer D, but containing 250 mM imidazole), respectively. The thioredoxin-fusion QCs were eluted from the first Ni-NTA column in a similar procedure to that described above, and the eluates were pooled and then digested with Factor Xa (0.2 unit/ml) (Novagen, Madison, Wis.) in a dialysis bag against buffer F (150 mM NaCl in 50 mM Tris-HCl, pH 8.0) at 25° C. for 2 days. The mature human QCs were obtained by loading the digests onto an additional Ni-NTA column followed by elution using a linear gradient of 0 to 30% of buffer E on buffer F. The purity of the human QCs was finally determined by SDS-polyacrylamide gel electrophoresis.

Figure 2:
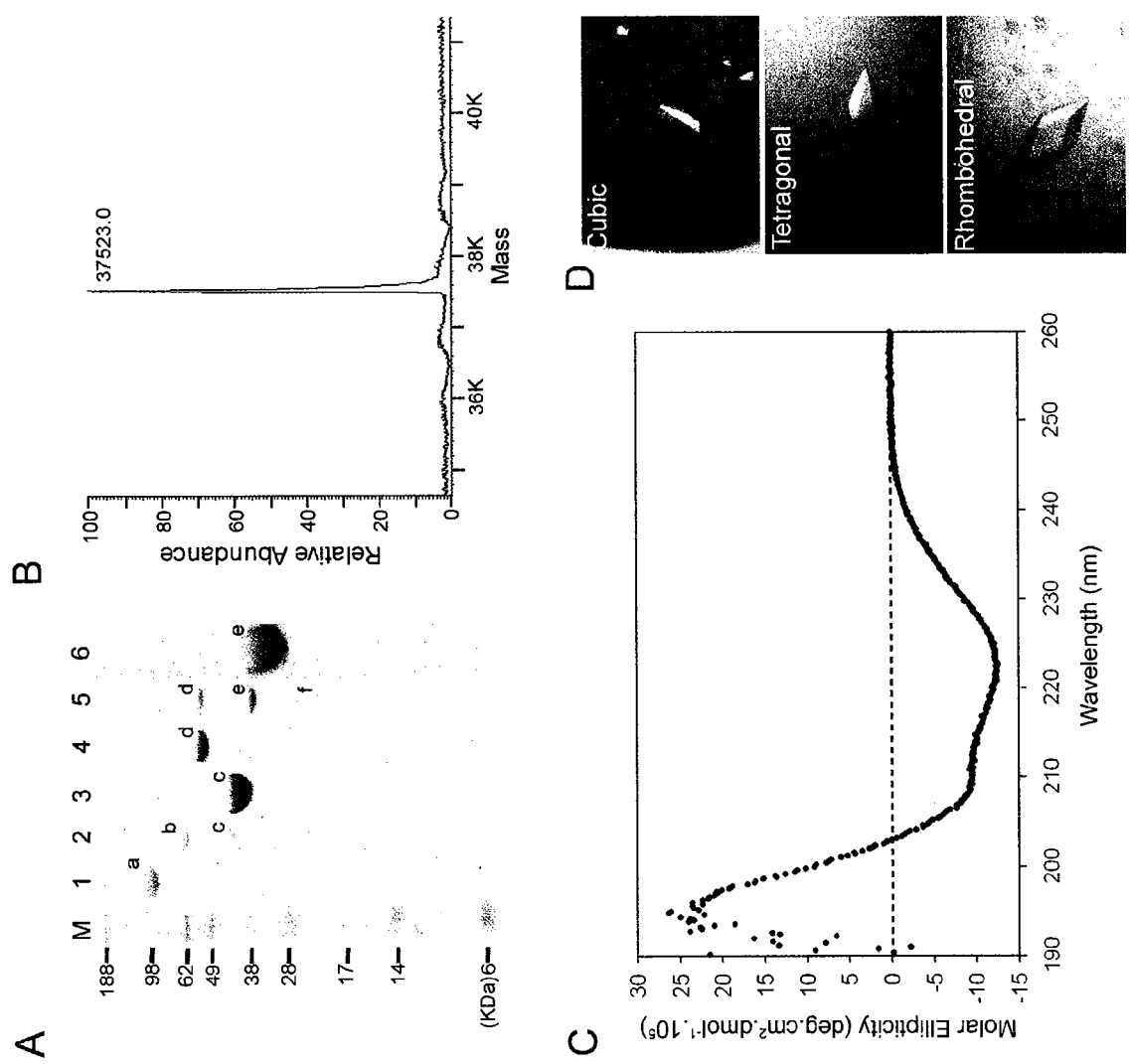
FIG. 2A is a graphical image showing SDS-PAGE analysis results of the recombinant human glutaminyl cyclase (QC)
FIG. 2B is a spectrum showing mass spectrometry analysis of the human QC.
FIG. 2C is a spectrum showing circular dichroism spectroscopy analysis of the human QC.
FIG. 2D is an image showing 3 forms of human QC crystals.

Referring to FIG. 2A, Nus-tagged human QCs and Trx-tagged human QCs were isolated from the crude extract of bacterial lysates and shown as band "a" and b and "d" in lanes 1 and 4, respectively. In other words, bands "a" and "d" represent human QCs fused to Nus and Trx fusion proteins, respectively, after first Ni-NTA column purification. The fusion proteins were cleaved in the digesting step, such as proteolytic digestion with thrombin or Factor Xa, producing two bands (b and c) of digestive products in lane 2 and three bands (d, e and f) of digestive products in lane 5.

The digested product of the Nus-tagged human QCs was subjected to an S protein-agarose column purification to eliminate cleaved Nus protein from the digested product, followed by an additional Ni-NTA column purification to yield final purified products of human QC with homogeneity of approximately 90%, as shown in lane 3. On the other hand, the digested product of the Trx-tagged human QCs was purified by an additional Ni-NTA column to yield the final purified products of human QC with nearly 100% homogeneity, as shown in lane 6.

Example 3

Mass Spectrometry Analysis

Mass spectrometry analysis was carried out on a Finnigan LCQ™ ion trap mass spectrometry (ThermoFinnigan, San Jose, Calif.) with electrospray ionization (ESI) interface. The ESI source was operated in positive ion mode. Sample solution was infused using an HPLC pump with loop injection. ESI operation conditions involved a spray voltage of 4.5 kV, a heated capillary temperature of 160° C., and a flow rate of 50 µl/min. The mass spectrometer was operated in full-scan profile mode, scan range from mass-to-charge (m/z) of 150 to 2000. Data acquisition and analysis were performed with Xcalibur (version 1.3, ThermoFinnigan, San Jose, Calif.) and BioWorks™ 3.0 (ThermoFinnigan, San Jose, Calif.).

As shown in FIG. 2B, mass spectrometry analysis revealed that the mature human QC had a molecular weight of 37523.0, which is consistent with the predicted molecular mass of 37515.5.

Example 4

Circular Dichroism Spectroscopy Analysis

Circular dichroism (CD) spectra of human QC (0.3 mg/ml) were measured at 25° C. on a Jasco J-715 spectropolarimeter using a 0.1 cm light-path cuvette. The mean of 10 scans between 190 and 260 nm was calculated and calibrated by subtraction of the buffer spectra (50 mM Tris-HCl, pH 8.0).

Referring to FIG. 2C, the circular dichroism spectrum of mature human QC corresponded well to the spectra of the proteins expressed in yeast and insect cell systems.

Example 5

Peptide Synthesis

The peptide [Gln$^1$]-TRH, with a C-terminal amide, was synthesized by standard FMOC peptide chemistry. After cleavage from the resin, the peptides were lyophilized and then purified by reversed phase High Performance Liquid Chromatography (HPLC). Purified peptides were verified by N-terminal sequencing and mass spectrometry.

Example 6

QC Activity Analysis and QC Inhibitor Assay

QC activity was analyzed based on reverse-phase HPLC and spectrophotometric measurement. In the case of HPLC, a 30 µl reaction mixture containing 0.6 µM human QC and 14.8 mM [Gln$^1$]-TRH in 50 mM Tris-HCl, pH 8.0 was incubated at 25° C. for a variety of periods ranging from 0-20 min. A reaction without addition of human QC was provided as a control in the assay. Subsequently, a 20 µl aliquot of the mixture was subjected to HPLC analysis on a Waters liquid chromatograph using a $C_{18}$ column (Waters, Milford, Mass.). The bound materials were eluted by a three-step linear gradient of methanol containing 0.1% trifluoroacetic acid (TFA). The eluates were detected at 214 nm and identified by mass spectrometry and N-terminal sequencing.

For the spectrophotometric method, the 500 µl assay solutions consisted of 15 units glutamate dehydrogenase, 12 mM α-ketoglutarate, 0.6 mM NADH (a reduced form of NAD (nicotinamide adenine dinucleotide)) and varying concentrations of synthetic substrate in 50 mM Tris-HCl, pH 8.0. Reactions were started by the addition of QC (0.04 to 2.5 µg), and the activity was monitored by recording the decrease of NADH absorbance at 340 nm.

Figure 3:
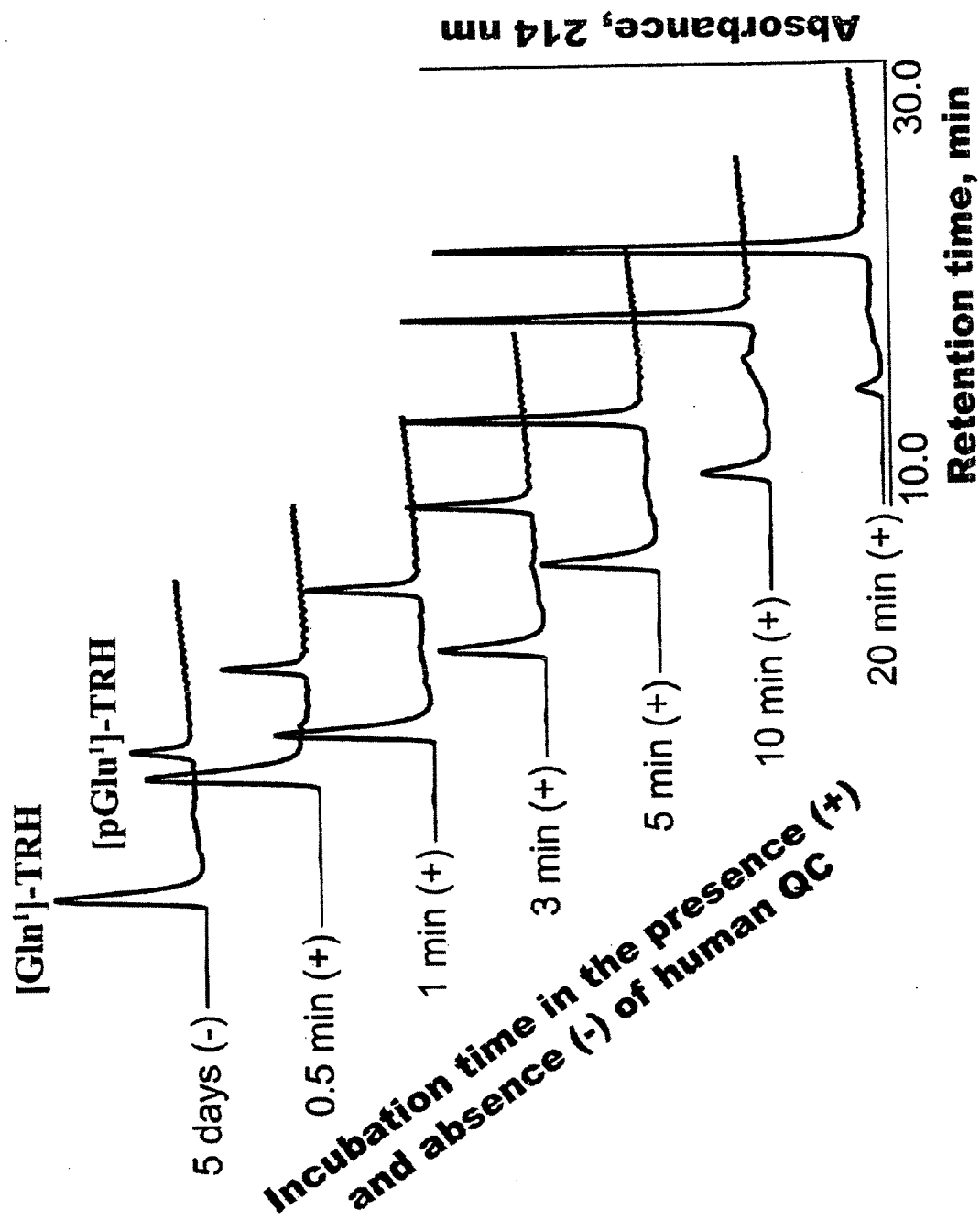
FIG. 3 is a spectrum showing analysis of QC activity on physiological substrate, $[Gln^1]$-TRH (Gln-His-Pro)

Recombinant human QCs expressed from either the pET 43.1a or the pET 32a constructs showed similar activities on synthetic substrates. The synthetic [Gln$^1$]-TRH (Gln-His-Pro), one of the putative physiological substrates of human QC, was used to analyze the QC activity of the recombinant protein based on the HPLC elution profile of the peptide. As shown in FIG. 3, [Gln$^1$]-TRH was almost completely converted by the enzyme into its corresponding product, [pGlu$^1$]-TRH, within 20 minutes. In contrast, less than 20% turnover was observed in the absence of human QC for 5 days under the assay condition (50 mM Tris-HCl, pH 8.0, at 25° C.).

The recombinant human QC was also active on other synthetic substrates, i.e., H-Gln-t-butyl ester and H-Gln-Gln- OH, based on the spectrophotometric experiment. The $K_m$ and $k_{cat}$ values determined for the recombinant protein of the invention were very similar to the human QC expressed in *Drosophila* S2 cells, as evident in Table 1. They were also comparable to the results of QC expressed in *Pichia pastoris* cells, except for the parameters analyzed on H-Gln-Gln-OH.

TABLE 1

Kinetic Parameters for Human QC Expressed in *E. coli*, Yeast and Insect Cell Systems

|  | $K_m$ (mM) | $k_{cat}$ (s$^{-1}$) | $k_{cat}/K_m$ (mM$^{-1}$s$^{-1}$) |
|---|---|---|---|
| *Escherichia coli* cell | | | |
| Gln-t-butyl ester | 4.1 ± 0.6[a] | 20.9 ± 2.1 | 5.1 ± 0.8 |
| Gln-Gln | 0.6 ± 0.1 | 8.6 ± 0.5 | 13.7 ± 0.5 |
| *Pichia pastoris* cell[b] | | | |
| Gln-t-butyl ester | 1.2 ± 0.1 | 6.7 ± 0.2 | 5.4 ± 0.2 |
| Gln-Gln | 0.1 ± 0.0 | 20.7 ± 0.2 | 140.0 ± 2.0 |
| *Drosophila* S2 cell[c] | | | |
| Gln-t-butyl ester | 6.7 ± 2.0 | 16.0 | 2.4 |
| Gln-Gln | 0.7 ± 0.4 | 10.0 | 14.3 |

[a] Mean ± SD (n = 2)
[b,c] Human QCs expressed in *Pichia pastoris* and *Drosophila* S2 cells were reported by Schilling et al. [Journal of Biological Chemistry, 384, 1583-1592 (2003)] and Booth, et al. [Protein Expression & Purification, 32, 141-146 (2003)], respectively.

For an inhibition test, the reaction composition was the same as described above, except for the addition of the inhibitor compound. Prior to the spectrophotometric analysis on a 96-well microplate, the enzyme was incubated with the inhibitor for 5 to 10 min. The concentrations of substrate (H-Gln-Gln-OH), human QC and inhibitor in the assay solution were 0.55 mM, 28.8 nM and 140 μM, respectively.

As listed in Table 2 below, 8 out of the 25 tested imidazole, triazole and tetrazole derivatives were presented as potent inhibitors of the recombinant human QC according to the invention, as determined by a quickly-screening procedure using a 96-well microplate.

TABLE 2

Effects of Imidazole, Triazole and Tetrazole Derivatives on Glutaminyl Cyclase Activity of the Recombinant Human QC

| Compound | Structure | QC activity (% of control) |
|---|---|---|
| None | | 100.0 |
| 1-benzylimidazole | 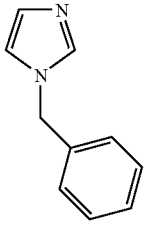 | 41.5 |
| N-ω-acetylhistamine | 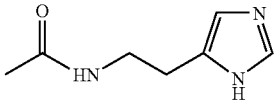 | 66.3 |
| 3-amino-1,2,4-triazole | 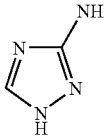 | 84.5 |
| 3,5-diamino-1,2,4-triazole | 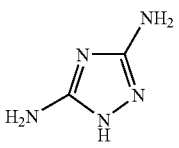 | 89.9 |

TABLE 2-continued

Effects of Imidazole, Triazole and Tetrazole Derivatives on Glutaminyl Cyclase Activity of the Recombinant Human QC

| Compound | Structure | QC activity (% of control) |
|---|---|---|
| 4-phenyl-1,2,4-triazoleine-3,5-dione | 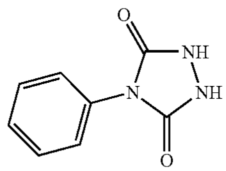 | 78.2 |
| nitron | 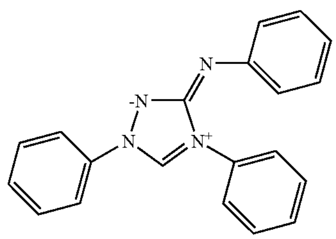 | 61.4 |
| ethyl 1H-tetrazole-5-acetate | 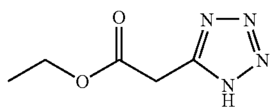 | 90.6 |
| 5-(methylthio)-1H-tetrazole | 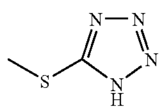 | 89.1 |

Example 7

Atomic Absorption Analysis

The zinc content of human QC was estimated by employing an atomic absorption spectrophotometer (Hitachi, Tokyo, Japan) as described previously. The protein concentration was spectroscopically determined in 6.0 M guanidine hydrochloride using an extinction coefficient of 55190 $M^{-1}$ $cm^{-1}$ at 280 nm estimated from the amino-acid sequence of human QC.

Figure 4:
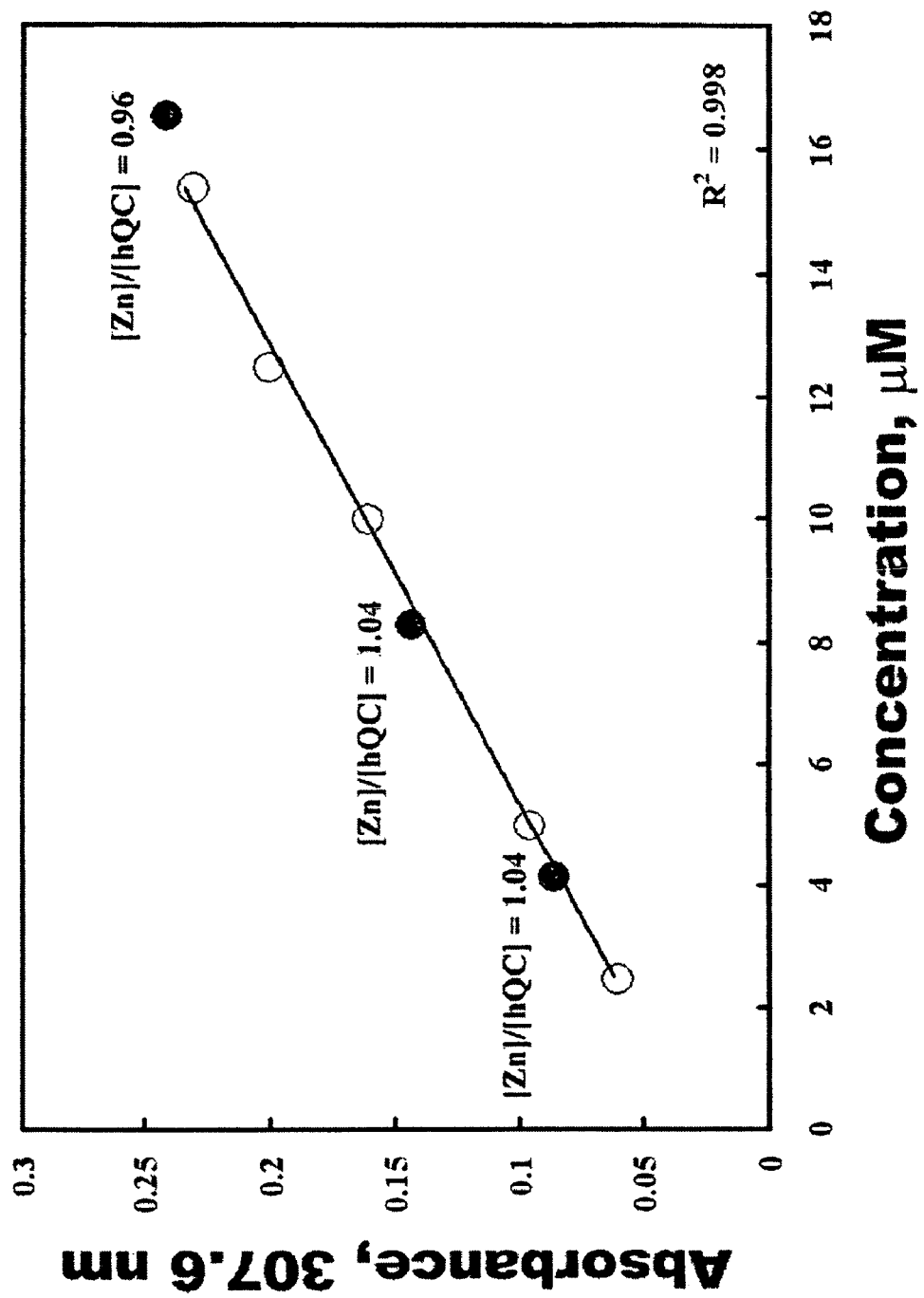
FIG. 4 is a line graph showing analysis of the zinc ion content in the human QC.

As shown in FIG. 4, the zinc to human QC molar ratio, being approximately 1, was determined in triplicate at various protein concentrations. The zinc concentration in the protein solutions was estimated according to the absorbance at zinc wavelength of 307.6 nm and a standard curve made by using zinc sulfate in a high correlation coefficient of 0.998. The protein concentration was carefully quantified based on the extinction coefficient. Therefore, the human QC obtained according to the invention was demonstrated to contain one zinc ion or single zinc ion per protein molecule as analyzed by atomic absorption spectrophotometry.

Example 8

Crystallization and Data Collections

The recombinant human QC as obtained was concentrated to 8 to 10 mg/ml using an ultra-filtration membrane YM-10 (Millipore, Billerica, Mass.). The screening for the human QC crystals was achieved using the crystallization kits from Hampton Research Co. (Hampton, Laguna Niguel, Calif.) by the method of hanging drop vapor diffusion. Cubic crystals for the pET 43.1a products were obtained using equal volume of the protein solution and a reservoir containing 30% PEG 4000 and 0.2 M $MgCl_2$ in 0.1 M Tris-HCl, pH 8.5. For the tetragonal crystals of mature human QC, the reservoir consisted of 20% PEG MME 550 and 0.1 M NaCl in 0.1 M Bicine, pH 9.0. For the rhombohedral crystals of mature human QC, the reservoir was 1.8 M $(NH_4)_2SO_4$ and 4% dioxane in 0.1 M MES, pH 6.5.

X-ray diffraction experiments were performed at the Institute of Biological Chemistry, Academia Sinica (Taipei, Taiwan) using MSC MicroMax 002 (Rigaku, Japan) equipped with an R-AXIS IV++ image-plate detector (Rigaku, Japan). Prior to mounting on the X-ray machine, the crystals were briefly soaked in mother liquor containing 20 to 25% glycerol (v/v) as cryoprotectants. Diffraction data were processed and scaled using the HKL package and are listed in Table 3.

After a number of crystallization screenings, three human QC crystals, which belong to cubic, tetragonal and rhombohedral forms, were obtained and are shown in FIG. 2D. The cubic crystals were grown using the purified products of human QC from pET 43.1a-based vector construct, while the others were made from the purified products of human QC from pET 32a-based vector construct. Among these, the rhombohedral crystals were best to diffract X-ray, as evident in Table 3 below.

TABLE 3

Statistics of X-ray Data Collections

| Crystal form | Cubic | Tetragonal | Rhombohedral |
|---|---|---|---|
| Space group | F432 | P422 | R32 |
| Resolution (Å) | 30.0-3.10 | 25.0-2.25 | 50.0-1.78 |

TABLE 3-continued

Statistics of X-ray Data Collections

| Crystal form | Cubic | Tetragonal | Rhombohedral |
|---|---|---|---|
| Cell dimensions (Å) | a = b = c = 273.47 | a = b = 70.04 c = 198.39 | a = b = 119.26 c = 333.73 |
| Unique reflections | 16234 | 23825 | 84584 |
| Redundancy | 4.5 | 4.7 | 4.2 |
| Completeness (%) | 98.8 (97.3) | 97.7 (99.8) | 96.4 (94.1) |
| I/σ(I) | 11.3 (2.6) | 33.7 (4.1) | 29.2 (2.6) |
| $R_{merge}$ (%) | 12.0 (51.7) | 5.6 (57.1) | 4.9 (59.8) |
| $^a$Mol/a.u. | 2 | 1 | 2 |
| $^b V_m$ | 2.839 | 3.243 | 3.019 |

$^a$Number of molecules per asymmetric unit.
$^b$Matthews coefficient.

Additionally, fluorescence peaks emitted from the tetragonal and rhombohedral crystals were found using synchrotron radiation with X-ray energy set on the zinc-absorption range (data not shown). This result was consistent with the result of the atomic-absorption experiment described in Example 7 above.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

the FCS, wherein a soluble QC is expressed in an *Escherichia coli* (*E. coli*) cell transformed with the vector.

2. The vector of claim 1, wherein the QC is human QC.

3. The vector of claim 1, wherein x is 6.

4. The vector of claim 1 being a plasmid having an origin of replication that allows the plasmid to be replicated in the *E. coli* cell.

5. A transformed *E. coli* cell comprising the vector of claim 1.

6. A method of expressing a soluble glutaminyl cyclase (QC), comprising growing the transformed *E. coli* cell of claim 5 under conditions that allow expression of the fusion protein.

7. A method for obtaining a purified soluble glutaminyl cyclase (QC), comprising the steps of:
transforming the vector according to claim 1 into the *E. coli* cell to obtain a transformed *E. coli* cell;
expressing the fusion protein in the transformed *E. coli* cell;
lysing the transformed *E. coli* cell to obtain a protein lysate containing the fusion protein;
loading the protein lysate onto a first Ni-affinity chromatography column in a first buffer comprising about 20 mM imidazole;
eluting the fusion protein from the first Ni-affinity chromatography column using a second buffer comprising about 250 mM imidazole to create a linear gradient of 0 to 100% of the imidazole;

---

---

We claim:

1. A vector comprising a nucleotide sequence encoding a fusion protein, wherein the fusion protein comprises, from the amino-terminus to the carboxyl-terminus, in the order, a thioredoxin (Trx) tag, a (His)$_6$-tag, a thrombin cleavage site (TCS), an S-tag, an enterokinase cleavage site (ECS), a linker and a glutaminyl cyclase (QC), wherein the linker is immediately adjacent to the amino-terminus of the QC, and the linker consists of a Factor Xa cleavage site (FCS) and at least one (His)$_x$-tag, wherein x is an integer of at least 6, and the (His)$_x$-tag is immediately adjacent to the amino-terminus of treating the eluted fusion protein with Factor Xa in a third buffer free of imidazole to obtain a digested solution containing the QC;
loading the digested solution onto a second Ni-affinity chromatography column; and
eluting the QC from the second Ni-affinity chromatography column with a linear gradient of 0 to 30% of the imidazole to obtain the purified soluble QC.

8. The method of claim 7, wherein the *E. coli* cell is an *Escherichia coli* BL21 cell.

* * * * *

SEQUENCE LISTING

```
<160> NUMBER OF SEQ ID NOS: 2

<210> SEQ ID NO 1
<211> LENGTH: 24
<212> TYPE: DNA
<213> ORGANISM: Homo sapiens

<400> SEQUENCE: 1
ggctgggaga gatggcaggc ggaa                                           24

<210> SEQ ID NO 2
<211> LENGTH: 24
<212> TYPE: DNA
<213> ORGANISM: Homo sapiens

<400> SEQUENCE: 2
ggatagatgt ttccacacag catt                                           24
```